United States Patent
Hämäläinen et al.

(10) Patent No.: US 12,345,637 B2
(45) Date of Patent: Jul. 1, 2025

(54) FLUID QUALITY MONITORING

(71) Applicant: UPONOR OYJ, Vantaa (FI)

(72) Inventors: Esa Hämäläinen, Nokia (FI); Tero Kesti, Tampere (FI); Teemu Heikkilä, Helsinki (FI); Vili Hätönen, Helsinki (FI); Oskari Lehto, Helsinki (FI); Joel Pyykkö, Helsinki (FI)

(73) Assignee: UPONOR OYJ, Vantaa (FI)

( * ) Notice: Subject to any disclaimer, the term of this patent is extended or adjusted under 35 U.S.C. 154(b) by 203 days.

(21) Appl. No.: 18/038,111

(22) PCT Filed: Dec. 10, 2021

(86) PCT No.: PCT/FI2021/050864
§ 371 (c)(1),
(2) Date: May 22, 2023

(87) PCT Pub. No.: WO2022/123121
PCT Pub. Date: Jun. 16, 2022

(65) Prior Publication Data
US 2024/0003808 A1    Jan. 4, 2024

(30) Foreign Application Priority Data
Dec. 11, 2020    (EP) .................................... 20213369

(51) Int. Cl.
*G01N 33/18*    (2006.01)
*G01N 21/45*    (2006.01)

(52) U.S. Cl.
CPC .......... *G01N 21/453* (2013.01); *G01N 33/18* (2013.01); *G01N 2201/1296* (2013.01)

(58) Field of Classification Search
CPC .......... G01N 33/18; G01N 2201/1296; G06N 3/088; G06N 3/045
See application file for complete search history.

(56) References Cited

U.S. PATENT DOCUMENTS

2019/0320934 A1    10/2019   Odry et al.

OTHER PUBLICATIONS

Meral Yurtsever, "Use of a convolutional neural network for the classification of microbeads in urban wastewater", 2018 (Year: 2018).*
Tomi Pitkäaho, "Focus prediction in digital holographic microscopy using deep convolutional neural networks", Feb. 10, 2019 (Year: 2019).*

(Continued)

*Primary Examiner* — Maurice C Smith
(74) *Attorney, Agent, or Firm* — CANTOR COLBURN LLP

(57) ABSTRACT

It is an objective to provide a fluid quality measurement device. According to an embodiment, a fluid quality measurement device is configured to: obtain a plurality of holograms, wherein each hologram in the plurality of holograms represents a microscopic object in a fluid sample; produce a latent space representation of each hologram using a trained autoencoder neural network; assign each hologram in the plurality of holograms to a class based on the latent space representation of the hologram; and produce a fluid sample fingerprint based on the assignment of the plurality of holograms into the plurality of classes.

18 Claims, 9 Drawing Sheets

(56) References Cited

OTHER PUBLICATIONS

Davide Abati, "Latent Space Autoregression for Novelty Detection", 2019 (Year: 2019).*
Elad Tzoreff, "Deep Discriminative Latent Space for Clustering", 2017 (Year: 2017).*
Beggel, Laura, et al. "Robust Anomaly Detection in Images Using Adversarial Autoencoders," Springer Nature Switzerland AG, U. Brefeld et al. (Eds.): ECML PKDD 2019, LNAI 11906, 2020, 17 pages.
Garaguly, Zoltan, et al. "Assessment of digital holographic image quality parameters," SAMI 2019, IEEE 17th World Symposium on Applied Machine Intelligence and Informatics, Jan. 24-26, 2019, Herl'any, Slovakia, 6 pages.
Janani, S. Dhiravida, et al. "Blood Cell Detection and Counting Using Convolutional Sparse Dictionary Learning," Proceeding of 2018 IEEE International Conference on Current Trends Toward Converging Technologies, Coimbatore, India (2018), 8 pages.
PCT International Search Report of the ISA/EPO mailed Mar. 18, 2022 for International Application No. PCT/FI2021/050864 filed Dec. 10, 2021, 4 pages.
Postnikov, Vladimir, et al., Chapter 5 "Holographic Sensors for Detection of Components in Water Solutions," INTECH, 2013, 26 pages.
Written Opinion of the International Searching Authority (ISA/EPO) mailed Mar. 18, 2022 in International Application No. PCT/FI2021/050864 filed Dec. 10, 2021, 9 pages.

* cited by examiner

1200

FLUID QUALITY MONITORING

TECHNICAL FIELD

The present disclosure relates to fluid quality monitoring, and more particularly to a fluid quality measurement device, a server, corresponding methods, and a fluid quality monitoring system.

BACKGROUND

Fluids, such as water, are almost never completely pure. Even cleanest natural waters and municipal tap waters can contain substantial amounts of dissolved and undissolved solids. Undissolved solids may be organic or inorganic particles such as clay particles, rust particles, humus particles etc. They may also be of biological origin, such as living and dead bacterial cells, algae, protozoa etc. In drinking water systems, these microscopic objects may originate from a water source, infrastructure or materials used in water production process, distribution pipe or storage tank walls, or from external material which enters the drinking water system due to a contamination event. Examples of contamination events include mixing of potable water and ground water, surface water or sewage due to a leakage in distribution pipe, or animals entering and drowning in water infrastructure such as a tank, reservoir or water tower. In some conditions, it is also possible that certain microbes that are naturally present in water in small quantities multiply in the water system in quantities that can cause infections. Precautions such as disinfection and chlorination of water are carried out by water utilities, but they may not always be effective. Effectiveness of some processes such as disinfection by UV light may also be hampered by presence of solid particles, which may shade harmful microbes from the effect of UV rays.

For the above-mentioned reasons, measuring and monitoring microscopic particles in water is important for ensuring that water production and distribution processes function as intended. The standard process for monitoring quality of municipal drinking water is based on collecting samples in specified locations and time intervals and transporting them to a laboratory for analysis. Both temporal and geographical coverage of this method is obviously limited, and there is a need for continuous, real-time monitoring method for drinking water production and distribution systems.

Turbidity meters are commonly used for real-time monitoring of suspended solid particles present in fluids. However, a turbidity meter only gives a single value related to total amount of suspended particles in the fluid, and no indication of what those particles might be. More expensive laser particle counters can also provide particle size information and can be used to monitor particle concentration in several size fractions. However, harmless particles present in water such as clay or silt may be of same size as unwanted and even harmful micro-objects such as fibres, bacteria, protozoa, algae etc.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter.

It is an objective to provide a fluid quality measurement device. The foregoing and other objectives are achieved by the features of the independent claims. Further implementation forms are apparent from the dependent claims, the description and the figures.

According to a first aspect, a fluid quality measurement device comprises at least one processor and at least one memory including computer program code, the at least one memory and the computer program code configured to, with the at least one processor, cause the fluid quality measurement device to: obtain a plurality of holograms, wherein each hologram in the plurality of holograms represents a microscopic object in a fluid sample; produce a latent space representation of each hologram in the plurality of holograms using a trained autoencoder neural network; assign each hologram in the plurality of holograms to a class in a plurality of classes based on the latent space representation of the hologram, wherein each class in the plurality of classes corresponds to a partition of the latent space; and produce a fluid sample fingerprint based on the assignment of the plurality of holograms into the plurality of classes, wherein the fluid sample fingerprint comprises an indication of a concentration of microscopic objects in the fluid sample for each class in the plurality of classes. The fluid quality measurement device can, for example, efficiently detect and classify microscopic objects corresponding to different classes in the fluid sample.

In an implementation form of the first aspect, the at least one memory and the computer program code are further configured to, with the at least one processor, cause the fluid quality measurement device to: provide the fluid sample fingerprint for transmission to a server and/or provide the fluid sample fingerprint to a user. The fluid quality measurement device can, for example, indicate the concentrations in different classes to a server and/or the user using the fluid sample fingerprint.

In a further implementation form of the first aspect, the autoencoder neural network comprises a variational autoencoder neural network or a convolutional variational autoencoder neural network. A variational autoencoder neural network may be able to produce a more stable latent space representation of a hologram. Further, a convolutional variational autoencoder neural network may be able to efficiently encode the holograms.

In a further implementation form of the first aspect, the at least one memory and the computer program code are further configured to, with the at least one processor, cause the fluid quality measurement device to provide a sample hologram from the plurality of holograms for at least one class in the plurality of classes for transmission to a server and/or provide a sample hologram from the plurality of holograms for at least one class in the plurality of classes to a user. The fluid quality measurement device can, for example, enable the server to perform further analysis based on the sample hologram(s) and/or adjust the convolutional neural network and/or the latent space partitions based on the sample hologram(s).

In a further implementation form of the first aspect, the at least one memory and the computer program code are further configured to, with the at least one processor, cause the fluid quality measurement device to provide a sample latent space representation of a hologram from the plurality of holograms for at least one class in the plurality of classes for transmission to a server. The fluid quality measurement device can, for example, enable the server to perform further analysis based on the sample latent space representation(s)

and/or adjust the convolutional neural network and/or the latent space partitions based on the sample latent space representation(s).

In a further implementation form of the first aspect, the at least one memory and the computer program code are further configured to, with the at least one processor, cause the fluid quality measurement device to: assign each hologram in the plurality of holograms to a class in a second plurality of classes using a trained convolutional neural network, wherein the second plurality of classes comprises at least one class of interest; and compute an indication of a concentration of microscopic objects corresponding to the at least one class of interest in the fluid sample based on the assignment of the plurality of holograms into the second plurality of classes. The convolutional neural network can detect microscopic object corresponding to the at least one class of interest even in small concentrations. These microscopic objects may indicate contamination of the fluid sample even in small concentrations.

In a further implementation form of the first aspect, the at least one memory and the computer program code are further configured to, with the at least one processor, cause the fluid quality measurement device to: provide the indication of the concentration of microscopic objects corresponding to the at least one class of interest in the fluid sample for transmission to a server and/or provide the indication of the concentration of microscopic objects corresponding to the at least one class of interest in the fluid sample to a user.

In a further implementation form of the first aspect, the fluid quality imaging device further comprises an imaging unit configured to produce the plurality of holograms using digital holographic microscopy. The imaging unit may be able to, for example, provide the holograms in an efficient fashion.

According to a second aspect, a server comprises at least one processor and at least one memory including computer program code, the at least one memory and the computer program code configured to, with the at least one processor, cause the server to: receive a fluid sample fingerprint from a fluid quality measurement device, wherein the fluid sample fingerprint comprises an indication of a concentration of microscopic objects in a fluid sample for each class in a plurality of classes; compare the fluid sample fingerprint to at least one preconfigured criterion; in response to the fluid sample fingerprint not meeting the preconfigured criterion, provide an anomaly notification. The server may be able to, for example, identify an anomaly in a fluid sample based on the fluid sample fingerprint.

In an implementation form of the second aspect, the at least one memory and the computer program code are further configured to, with the at least one processor, cause the server to compare the fluid sample fingerprint to at least one preconfigured criterion by performing: produce a feature space representation of the fluid sample fingerprint, wherein each dimension of the feature space corresponds to a class in the plurality of classes; and compare the feature space representation of the fluid sample fingerprint to a feature space representation of at least one reference fingerprint. The server may be able to, for example, efficiently compare the fluid sample fingerprint and the at least one reference fingerprint using the feature space representation.

In a further implementation form of the second aspect, the at least one memory and the computer program code are further configured to, with the at least one processor, cause the server to compare the feature space representation of the fluid sample fingerprint to a feature space representation of the at least one reference fingerprint by calculating a distance metric between the fluid sample fingerprint and the at least one reference fingerprint. The server may be able to, for example, efficiently compare the fluid sample fingerprint and the at least one reference fingerprint using the distance metric.

In a further implementation form of the second aspect, the at least one memory and the computer program code are further configured to, with the at least one processor, cause the server to: compare the calculated distance metric to a preconfigured maximum distance metric; and in response to the calculated distance metric being greater than the preconfigured maximum distance metric, provide the anomaly notification. The server may be able to, for example, efficiently detect an anomaly in the fluid sample based on the fluid sample fingerprint and the distance metric.

In a further implementation form of the second aspect, the at least one memory and the computer program code are further configured to, with the at least one processor, cause the server to compare the fluid sample fingerprint to at least one preconfigured criterion by performing: compare the indication of the concentration of microscopic objects in the fluid sample of each class in the plurality of classes to a corresponding preconfigured maximum value; and in response to the indication of the concentration of microscopic objects being greater than the corresponding preconfigured maximum value in at least one class, provide the anomaly notification. The server may be able to, for example, efficiently detect an anomaly in the fluid sample even in situations where only one class comprises an anomaly.

According to a third aspect, a fluid quality monitoring system comprises at least one fluid quality measurement device according to the first aspect and a server according to the second aspect.

According to a fourth aspect, a method for fluid quality measurement comprises: obtaining a plurality of holograms, wherein each hologram in the plurality of holograms represents a microscopic object in a fluid sample; producing a latent space representation of each hologram in the plurality of holograms using a trained autoencoder neural network; assigning each hologram in the plurality of holograms to a class in a plurality of classes based on the latent space representation of the hologram, wherein each class in the plurality of classes corresponds to a partition of the latent space; and producing a fluid sample fingerprint based on the assignment of the plurality of holograms into the plurality of classes, wherein the fluid sample fingerprint comprises an indication of a concentration of microscopic objects in the fluid sample for each class in the plurality of classes.

In an implementation form of the fourth aspect, the method further comprises and providing the fluid sample fingerprint for transmission to a server and/or providing the fluid sample fingerprint to a user.

In a further implementation form of the fourth aspect, the autoencoder neural network comprises a variational autoencoder neural network or a convolutional variational autoencoder neural network.

In a further implementation form of the fourth aspect, the method further comprises providing a sample hologram from the plurality of holograms for at least one class in the plurality of classes for transmission to a server and/or providing a sample hologram from the plurality of holograms for at least one class in the plurality of classes to a user.

In a further implementation form of the fourth aspect, the method further comprises providing a sample latent space representation of a hologram from the plurality of holograms for at least one class in the plurality of classes for transmission to a server.

In a further implementation form of the fourth aspect, the method further comprises: assigning each hologram in the plurality of holograms to a class in a second plurality of classes using a trained convolutional neural network, wherein the second plurality of classes comprises at least one class of interest; computing an indication of a concentration of microscopic objects corresponding to the at least one class of interest in the fluid sample based on the assignment of the plurality of holograms into the second plurality of classes.

In a further implementation form of the fourth aspect, the method further comprises providing the indication of the concentration of microscopic objects corresponding to the at least one class of interest in the fluid sample for transmission to a server and/or providing the indication of the concentration of microscopic objects corresponding to the at least one class of interest in the fluid sample to a user.

In a further implementation form of the fourth aspect, the obtaining the plurality of holograms comprises obtaining the plurality of holograms using digital holographic microscopy.

According to a fifth aspect, a method for fluid quality monitoring comprises: receiving a fluid sample fingerprint from a fluid quality measurement device, wherein the fluid sample fingerprint comprises an indication of a concentration of microscopic objects in a fluid sample for each class in a plurality of classes; comparing the fluid sample fingerprint to at least one preconfigured criterion; in response to the fluid sample fingerprint not meeting the preconfigured criterion, providing an anomaly notification.

In an implementation form of the fifth aspect, the comparing the fluid sample fingerprint to at least one preconfigured criterion comprises: producing a feature space representation of the fluid sample fingerprint, wherein each dimension of the feature space corresponds to a class in the plurality of classes; and comparing the feature space representation of the fluid sample fingerprint to a feature space representation of at least one reference fingerprint.

In a further implementation form of the fifth aspect, the comparing the feature space representation of the fluid sample fingerprint to a feature space representation of the at least one reference fingerprint comprises calculating a distance metric between the fluid sample fingerprint and the at least one reference fingerprint.

In a further implementation form of the fifth aspect, the method further comprises: comparing the calculated distance metric to a preconfigured maximum distance metric; and in response to the calculated distance metric being greater than the preconfigured maximum distance metric, providing the anomaly notification.

In a further implementation form of the fifth aspect, the comparing the fluid sample fingerprint to at least one preconfigured criterion comprises: comparing the indication of the concentration of microscopic objects in the fluid sample of each class in the plurality of classes to a corresponding preconfigured maximum value; and in response to the indication of the concentration of microscopic objects being greater than the corresponding preconfigured maximum value in at least one class, providing the anomaly notification.

According to a sixth aspect, a computer program product comprises program code configured to perform the method according to the fourth aspect or the fifth aspect when the computer program product is executed on a computer.

Many of the attendant features will be more readily appreciated as they become better understood by reference to the following detailed description considered in connection with the accompanying drawings.

DESCRIPTION OF THE DRAWINGS

In the following, example embodiments are described in more detail with reference to the attached figures and drawings, in which.

In the following, like reference numerals are used to designate like parts in the accompanying drawings.

DETAILED DESCRIPTION

In the following description, reference is made to the accompanying drawings, which form part of the disclosure, and in which are shown, by way of illustration, specific aspects in which the present disclosure may be placed. It is understood that other aspects may be utilised, and structural or logical changes may be made without departing from the scope of the present disclosure. The following detailed description, therefore, is not to be taken in a limiting sense, as the scope of the present disclosure is defined by the appended claims.

For instance, it is understood that a disclosure in connection with a described method may also hold true for a corresponding device or system configured to perform the method and vice versa. For example, if a specific method step is described, a corresponding device may include a unit to perform the described method step, even if such unit is not explicitly described or illustrated in the figures. On the other hand, for example, if a specific apparatus is described based on functional units, a corresponding method may include a step performing the described functionality, even if such step is not explicitly described or illustrated in the figures. Further, it is understood that the features of the various example aspects described herein may be combined with each other, unless specifically noted otherwise.

Figure 1:
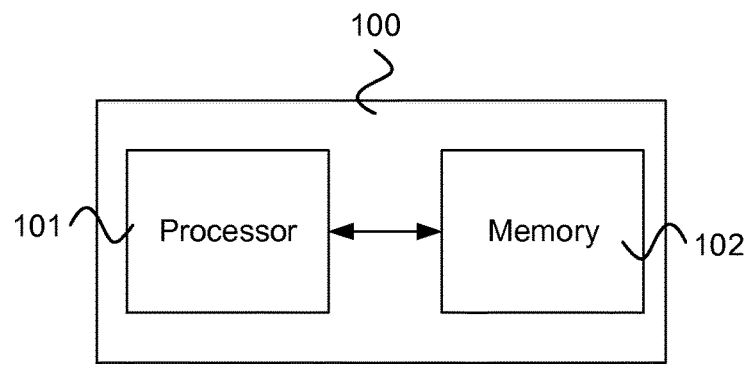
FIG. 1 illustrates a schematic representation of a fluid quality measurement device according to an embodiment.

FIG. 1 illustrates a schematic representation of a fluid quality measurement device 100 according to an embodiment.

According to an embodiment, the fluid quality measurement device 100 comprises at least one processor 101 and at least one memory 102 including computer program code.

The at least one memory 102 and the computer program code may be configured to, with the at least one processor 101, cause the fluid quality measurement device 100 to obtain a plurality of holograms. Each hologram in the plurality of holograms may represent a microscopic object in a fluid sample.

The fluid may be, for example, water, oil, or any other liquid.

Herein, a hologram of an object may refer to a two-dimensional image formed by the interference of light from a laser or other coherent light source, wherein at least part of the light scatters from the object and the scattered and unscattered light interfere and form an interference pattern. Such a two-dimensional recording of the interference pattern comprises three-dimensional information about the object. A hologram may thus refer to a photographic recording of a light field.

The microscopic object may be of foreign origin. The expression "of foreign origin" may refer to that the microscopic object is not formed of the fluid to be investigated itself. Such objects are thus formed of materials, such as rust or sand, different of the material(s) of the fluid itself so that the objects are carried within or by the fluid. They may originate, for example, from the materials of pipes or containers in which the fluid is conveyed or stored. Microscopic particles of the materials of such systems may be released to the fluid, for example, in result of a pipe breakage or equipment failure. Alternatively, microscopic objects of foreign origin may originate from foreign bodies or contaminants ended up within such pipes or containers. In the case of water supply systems, for example, such foreign body producing microbes into the water may be a dead animal.

In the case of water supply, distribution, or use systems and networks, microbes not normally present may be, for example, various bacteria, such as bacteria belonging to coliform or *Legionella* groups and cyanobacteria, protozoa such as *Giardia lamblia*, or various types of algae.

On the other hand, from the physical properties point of view, microscopic objects of foreign origin have typically, for example, a refractive index differing from that of the fluid. This enables detection of such objects by means of, for example, optical sensing. The fluid quality measurement device 100 can utilise this in that the detection of the microscopic objects is based on scattering of light by the microscopic objects due to the difference between the refractive indices of the microscopic objects and the fluid.

From dimensional point of view, "microscopic" objects refer to objects having their characteristic dimensions, such as maximum diameter, length, or width, in the range of 0.1, 0.5 or 1.0 to 50 or 100 μm. Objects with so small characteristic dimensions are not visible to human eye, so they cannot be detected visually. On the other hand, holograms formed by that sized objects are detectable by image sensor having a reasonably small size. Further, with such micrometre scale characteristic dimensions, objects scatter light mainly forward, thereby enabling efficient detection by in-line holography.

Obtaining a plurality of holograms may comprise, for example, performing such optical imaging that the holograms are produced as a result or obtaining the holograms from another device/unit/module.

The fluid sample may comprise a sample of flowing fluid, such as fluid in a pipe, or a sample of still fluid, such as fluid in a cuvette or other sample volume.

The fluid quality measurement device 100 may produce a latent space representation of each hologram in the plurality of holograms using a trained autoencoder neural network (NN).

Herein, the term "neural network" is used to refer to an artificial neural network.

The autoencoder NN can be pre-trained to encode each hologram into a latent space representation. The autoencoder NN may also be referred to simply as an autoencoder. The latent space representation may also be referred to as a reduced data set representation, a compressed data set representation, or similar.

The fluid quality measurement device 100 may be configured to reconstruct one or more images of a microscopic object from each hologram and feed the reconstructed one or more images to the autoencoder NN. Alternatively, the fluid quality measurement device 100 may feed the holograms to the autoencoder NN without image reconstruction. This has the advantage that computational resources do not need to be used for image reconstruction and the autoencoder NN can directly utilise the three-dimensional information in the holograms.

Herein, a latent space representation of an object may refer to a representation of the object in latent space. A latent space may refer to an abstract multi-dimensional space, wherein dimensions of the latent space correspond to features of the object. Typically, these features cannot be interpreted to directly correspond to distinct physical features, such as size, of the object, such as a hologram or the microscopic object represented by the hologram. Rather, these features encode information about the object that can be used to, for example, classify the object. The autoencoder NN learns the encoding during training of the autoencoder NN via appropriate training data.

The fluid quality measurement device 100 may assign each hologram in the plurality of holograms to a class in a plurality of classes based on the latent space representation of the hologram. Each class in the plurality of classes may correspond to a partition of the latent space.

The plurality of classes may have been generated using a clustering algorithm after training the autoencoder NN. Experimental data as training data and a suitable clustering algorithm can be used to partition the latent space in an unsupervised manner. The clustering algorithm can define a set of boundaries so that each partition in the latent space represents a different kind of microscopic object detected in the experimental data. Based on large amount of experimental data, latent space partitions can be combined (agglomerated), adjusted, or added to get an optimized set of partitions. Each such partition can correspond to a class in the plurality of classes.

The fluid quality measurement device 100 may produce a fluid sample fingerprint based on the assignment of the plurality of holograms into the plurality of classes, wherein the fluid sample fingerprint comprises an indication of a concentration of microscopic objects in the fluid sample for each class in the plurality of classes.

Herein, an indication of concentration of a microscopic object may refer to any quantity that correlates with and/or can be used to compute such a concentration. For example, an indication of concentration of a microscopic object in a class may comprise simply the number of microscopic objects corresponding to the class detected in the fluid sample. Based on the number of detected microscopic objects, the concentration of microscopic objects can be computed when the volume of the fluid sample is known.

Herein, the fluid sample fingerprint may also be referred to simply as a fingerprint.

The fluid quality measurement device 100 may provide the fluid sample fingerprint for transmission to a server and/or provide the fluid sample fingerprint to a user.

Herein, "provide for transmission" may comprise, for example, the fluid quality measurement device 100 transmitting the data in question or the fluid quality measurement device 100 providing the data to another device/module/unit that then transmits the data.

Herein, "provide to a user" may comprise, for example, the fluid quality measurement device 100 comprising a display and displaying the data in question to a user on the display or the fluid quality measurement device 100 providing the data to another device/module/unit that then displays the data to the user.

According to an embodiment, the fluid quality measurement device 100 is configured to provide a sample hologram from the plurality of holograms for at least one class in the plurality of classes for transmission to the server and/or provide a sample hologram from the plurality of holograms for at least one class in the plurality of classes to a user.

In some embodiments, the fluid quality measurement device 100 is configured to provide a sample hologram for each class in the plurality of classes from the plurality of holograms for transmission to the server. The fluid quality measurement device 100 may provide the sample holograms, for example, in the fluid sample fingerprint or separately from the fluid sample fingerprint. The sample holograms may be utilised for, for example, visually illustrating to a user the microscopic objects in the classes.

According to an embodiment, the fluid quality measurement device 100 is configured to provide a sample latent space representation of a hologram from the plurality of holograms for at least one class in the plurality of classes for transmission to the server.

The at least one processor 101 may comprise, for example, one or more of various processing devices, such as a central processing unit (CPU), a graphical processing unit (GPU), co-processor, a microprocessor, a processing unit, a digital signal processor (DSP), a processing circuitry with or without an accompanying DSP, or various other processing devices including integrated circuits such as, for example, an application specific integrated circuit (ASIC), a field programmable gate array (FPGA), a microprocessor unit (MCU), a hardware accelerator, such as a neural network accelerator, a special-purpose computer chip, or the like.

The at least one memory 102 may be configured to store, for example, computer programs and the like. The at least one memory 102 may comprise one or more volatile memory devices, one or more non-volatile memory devices, and/or a combination of one or more volatile memory devices and non-volatile memory devices. For example, the at least one memory 102 may be embodied as magnetic storage devices (such as hard disk drives, floppy disks, magnetic tapes, etc.), optical magnetic storage devices, and semiconductor memories (such as mask ROM, PROM (programmable ROM), EPROM (erasable PROM), flash ROM, RAM (random access memory), etc.).

The fluid quality measurement device 100 may further comprise other components not illustrated in the embodiment of FIG. 1. The fluid quality measurement device 100 may comprise, for example, an input/output bus for connecting the fluid quality measurement device 100 to other devices.

When the fluid quality measurement device 100 is configured to implement some functionality, some component and/or components of the fluid quality measurement device 100, such as the at least one processor 101 and/or the at least one memory 102, may be configured to implement this functionality. Furthermore, when the at least one processor 101 is configured to implement some functionality, this functionality may be implemented using program code comprised, for example, in the at least one memory 102.

Figure 2:
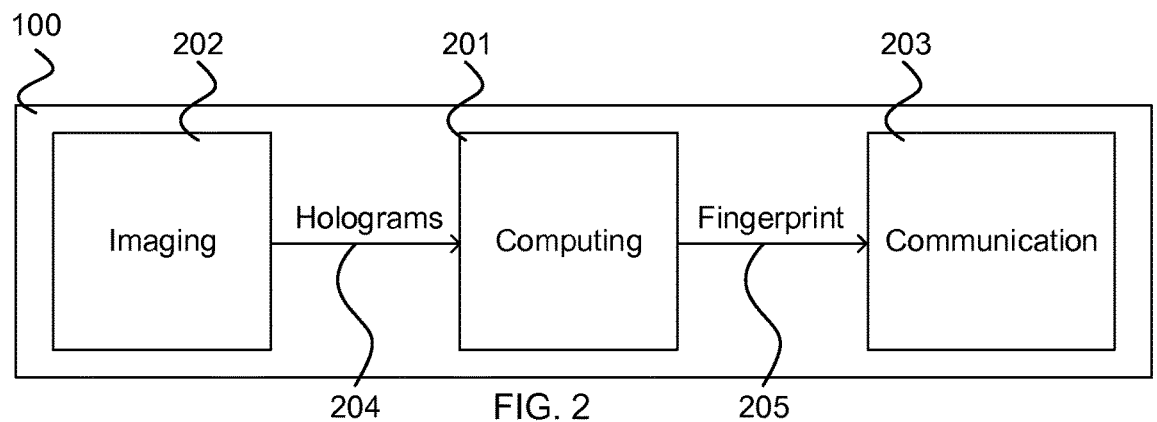
FIG. 2 illustrates a schematic representation of a fluid quality measurement device according to another embodiment.

FIG. 2 illustrates a schematic representation of a fluid quality measurement device 100 according to another embodiment.

In the embodiment of FIG. 2, the fluid quality measurement device 100 comprises a computing unit 201, an imaging unit 202, and a communication unit 203. The computing unit 201 may comprise the at least one processor 101 and the at least one memory 102. Thus, the computing unit 201 may be configured to implement any computational functionality of the fluid quality measurement device 100 disclosed herein.

It should be appreciated that the units 201, 202, 203 illustrated in the embodiment of FIG. 2 are only meant to illustrate the functionality of the fluid quality measurement device 100. Thus, the units 201, 202, 203 may not be implemented as distinct physical units in the fluid quality measurement device 100. For example, in some embodiments, the functionality of the computing unit 202 and of the communication unit 203 may be implemented using a single physical unit, such as a system on a chip (SoC).

In other embodiments, the fluid quality measurement device 100 may comprise only the computing unit 101 and the imaging unit 102. The communication unit 103 may be embodied in another device that may be coupled to the fluid quality measurement device 100.

The imaging unit 202 may be configured to produce the plurality of holograms 204 using, for example, digital holographic microscopy (DHM) or some other imaging procedure. The imaging unit 202 can then provide the plurality of holograms 204 to the computing unit 201.

The computing unit 201 can provide the fluid sample fingerprint 205 to the communication unit 203 for transmission. The communication unit 203 may transmit the fluid sample fluid sample fingerprint 205 to, for example, a server or any other device for analysis.

The communication unit 203 may be configured to transmit data to and receiver data from other devices using, for example, any wired or wireless communication technology, such as Ethernet, Wifi, 3G, 4G LTE, and/or 5G NR.

Figure 3:
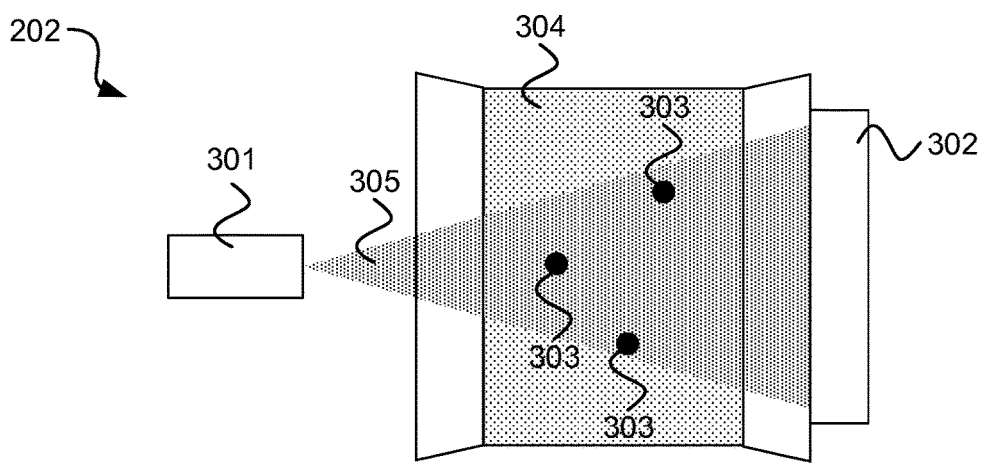
FIG. 3 illustrates a schematic representation of an imaging unit according to an embodiment.

FIG. 3 illustrates a schematic representation of an imaging unit 202 according to an embodiment.

The imaging unit 202 may comprise a camera sensor 302 and an illuminating arrangement 301. The imaging unit 202 may further comprise other components not illustrated in the embodiment of FIG. 3. For example, the imaging unit 202 may comprise a processor or other computing means configured to process images obtained from the camera sensor 302.

The imaging unit 202 may comprise a sample volume for receiving a fluid sample 304 possibly containing microscopic objects 303. The illuminating arrangement 301 may be configured to emit coherent light 305 and illuminate the fluid sample 304 received in the sample volume by the coherent light 305. When illuminating the sample volume by the coherent light 305, the possible microscopic objects 303 therein scatter part of the light 305, and the scattered and non-scattered portions of the illuminating light 305 interfere so as to form interference fringes behind the microscopic objects 303. The image sensor 302 can be positioned and configured to capture image frames by receiving the light propagated across the sample volume.

The illuminating arrangement 301 may comprise any appropriate light source, such as a laser diode, capable of producing coherent light. The light may have wavelength(s), for example, in the range of 350 to 500 nanometres, without being limited to that range. The illuminating arrangement 301 may further comprise any appropriate optical elements configured to guide the emitted coherent light 305 towards the sample volume to illuminate the fluid sample 304.

The camera sensor 302 may comprise a light sensitive component or element capable of capturing digital image frames. The camera sensor 302 may comprise, for example, a complementary metal oxide semiconductor (CMOS) sensor or any other appropriate type of sensor element as a light detection imaging element.

According to an embodiment, the imaging unit 202 is configured to perform digital holographic microscopy (DHM). In DHM, the light wave front information originating from the object is digitally recorded as a hologram. DHM is capable of both counting, sizing, and imaging of microscopic objects 303 in the fluid sample 304. Images of microscopic objects 303 can be recorded as holograms that contain three-dimensional shape information of the microscopic objects 303. One advantage of the DHM is the simplicity and robustness of the optical setup, requiring no microscopic lenses or other complex optical systems.

According to an embodiment, the imaging unit 202 is configured to produce the plurality of holograms 204 using DHM by illuminating the microscopic objects 303 with coherent light using the illuminating arrangement 301 and recording the resulting light wave front behind the microscopic objects 303 using the camera sensor 302.

In some embodiments, the imaging unit 202 may be configured to process, filter, and/or segment image frames obtained from the camera sensor 302. Thus, the imaging unit 202 can provide separate holograms 204 of individual microscopic objects 303 to the computing unit 201. In other embodiments, the imaging unit 202 may provide image frames from the camera sensor 302 to the computing unit 201 and the computing unit 201 may process, filter, and/or segment the image frames obtained from the camera sensor 302 in order to obtain separate holograms of the microscopic objects 303.

Figure 4:
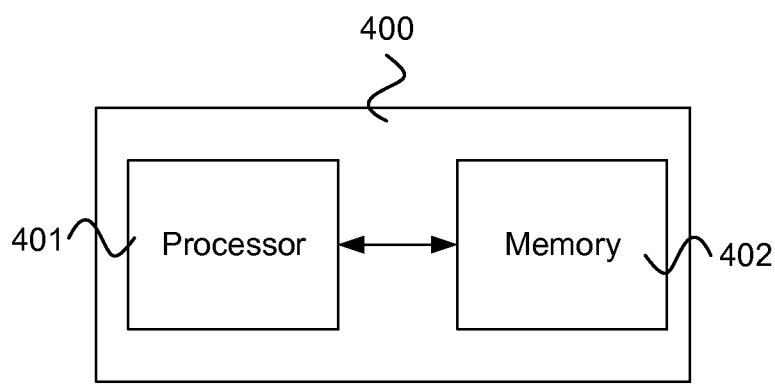
FIG. 4 illustrates a schematic representation of a server according to an embodiment.

FIG. 4 illustrates a schematic representation of a server 400 according to an embodiment.

According to an embodiment, the server 400 comprises at least one processor 401 and at least one memory 402 including computer program code.

The at least one memory 402 and the computer program code may be configured to, with the at least one processor 401, cause the server 400 to receive a fluid sample fingerprint 205 from a fluid quality measurement device 100, wherein the fluid sample fingerprint 205 comprises an indication of a concentration of microscopic objects in a fluid sample for each class in a plurality of classes.

Each class in the plurality of classes may correspond to one type of a microscopic object in the fluid sample. Any disclosure herein in relation to the fluid sample fingerprint produced by the fluid quality measurement device 100 may apply with respect to the fluid sample fingerprint received by the server 400.

The server 400 may be further configured to compare the fluid sample fingerprint to at least one preconfigured criterion.

The server 400 may be further configured to, in response to the fluid sample fingerprint not meeting the preconfigured criterion, provide an anomaly notification.

The server 400 may provide the anomaly notification to, for example, a user via a client device, such as a mobile phone or a computer. The anomaly notification may comprise, for example, any notification that indicates to the user that an anomaly has been detected in the fluid sample. The anomaly notification may also provide further information, such as type of the anomaly and/or information about the fluid quality measurement device 100 that transmitted the fluid sample fingerprint causing the anomaly notification, to the user.

The anomaly notification may also be referred to as a fluid anomaly notification, a fluid quality anomaly notification, or similar.

According to an embodiment, the server 400 is further configured to produce a feature space representation of the fluid sample fingerprint, wherein each dimension of the feature space corresponds to a class in the plurality of classes. The server 400 may compare the feature space representation of the fluid sample fingerprint to a feature space representation of at least one reference fingerprint.

A feature space may refer to an abstract multi-dimensional space, wherein dimensions of the feature space correspond to classes in a fluid sample fingerprint. The indication of concentration of microscopic objects in a class can be used as the coordinate of the fluid sample fingerprint in a corresponding dimension of the feature space. Thus, a fluid sample fingerprint can be represented as a point in the feature space.

The at least one reference fingerprint may correspond to a known good fluid sample, such as a fingerprint obtained from a water treatment facility. The server 400 may, for example, separate known good fluid samples by clustering received fluid sample fingerprints in the feature space and calculate a suitable distance metric to indicate how much the current fluid quality, indicated by the fluid sample fingerprint, differs from known good conditions.

The server 400 may compare the feature space representation of the fluid sample fingerprint to a feature space representation of the at least one reference fingerprint by calculating a distance metric between the fluid sample fingerprint and the at least one reference fingerprint.

The distance metric may quantify the distance between the fluid sample fingerprint and the at least one reference fingerprint in the feature space. The distance metric may be, for example, Euclidian distance or any other appropriate distance metric. It should be appreciated that since the distance metric is measured in the feature space, the term "distance" should not be interpreted as corresponding to any physical distance or any other strictly physical quantity.

The server 400 may compare the calculated distance metric to a preconfigured maximum distance metric and, in response to the calculated distance metric being greater than the preconfigured maximum distance metric, provide the anomaly notification.

The preconfigured maximum distance metric may be set, for example, manually or automatically based on previously obtained data, such as fluid sample fingerprints from the same fluid quality measurement device 100 and/or other fluid quality measurement devices 100.

Alternatively, the server 400 may compare the fluid sample fingerprint to at least one preconfigured criterion by comparing the indication of the concentration of microscopic objects in the fluid sample of each class in the plurality of classes to a corresponding preconfigured maximum value. The server 400 may then, in response to the indication of the concentration of microscopic objects being greater than the corresponding preconfigured maximum value in at least one class, provide the anomaly notification.

For example, the server 400 may compare microscopic object concentrations in each fingerprint class to maximum values based on statistical microscopic object concentration values measured during a calibration period. If the concentration in greater than a corresponding maximum value obtained based on the calibration, the server 400 may provide the anomaly notification.

According to an embodiment, the server 400 is configured to receive a sample hologram for at least one class in the plurality of classes from the fluid quality measurement device 100. The server 400 may be further configured to provide a visual illustration of the hologram to a user.

According to an embodiment, the server 400 is configured to receive a sample latent space representation of a hologram for at least one class in the plurality of classes from the fluid quality measurement device 100.

In some embodiments, the functionality of the server 400 may be implemented using a cloud computing system or other type of distributed computing system.

In some embodiments, the fluid quality measurement device 100 may be implemented as a stand-alone device. In such embodiments, the fluid quality measurement device 100 may be configured to implement any functionality of the server 400 disclosed herein. Thus, the fluid quality measurement device 100 may form the fluid quality fingerprint, compare the fluid quality fingerprint to at least one preconfigured criterion, and provide the anomaly notification to a user in response to the fluid sample fingerprint not meeting the preconfigured criterion.

Figure 5:
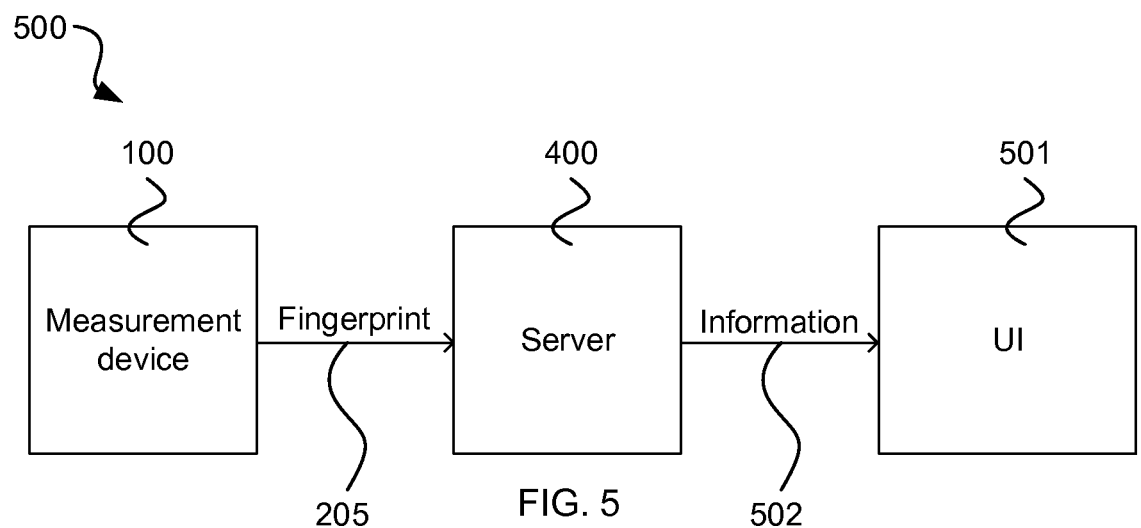
FIG. 5 illustrates a schematic representation of a fluid quality monitoring system according to an embodiment.

FIG. 5 illustrates a schematic representation of a fluid quality monitoring system 500 according to an embodiment.

According to an embodiment, the fluid quality monitoring system 500 comprises at least one fluid quality measurement device 100 and the server 400.

Any devices of the fluid quality monitoring system 500, such as the fluid quality measurement device 100, the server 400, and/or the device providing the UI 501 may transmit data to and/or receive data from other devices in the system 500 using, for example, any wired or wireless communication technology, such as Ethernet, Wifi, 3G, 4G LTE, and/or 5G NR or any combination thereof.

In some embodiments, the system 500 may comprise a plurality of fluid quality measurement devices 100 and each fluid quality measurement device 100 may communicate with the server 400. The server 400 may process information provided by the plurality of fluid quality measurement devices 100 as disclosed herein.

The system 500 may further comprise a user interface (UI) 501. The UI 501 may be implemented on, for example, a client device, such as a mobile phone or a computer. The UI 501 may be provided for example, as a web UI by the server 400. A user may be authenticated using such a web UI.

The server 400 may provide information 502 to a user via the UI 501. The information 501 may comprise, for example, anomaly notifications, historical data about fluid quality in measurement locations, fluid quality information via a map view, and/or view of data of a specific measurement location. Each measurement location may comprise one or more fluid quality measurement devices 100.

In normal operation, inference of the trained neural networks takes place in the fluid quality measurement device 100. The fluid quality measurement device 100 can transmit a fluid sample fingerprint 205 periodically, for example every 5 minutes, to the server 400. Additionally, the fluid quality measurement device 100 may transmit sample holograms and/or their latent representations for each fingerprint class to the server 400 for visualization and/or for optimising latent space partitioning and partition aggregation in order to produce an improved version of the system 500 at later point in time. This also makes it possible to retrain the autoencoder neural network used by the fluid quality measurement device 100 later with an even larger and/or more diverse dataset.

In the server 400, fluid sample fingerprints 205 received from fluid quality measurement devices 100 can be used to detect fluid quality anomalies. A new fluid sample fingerprint 205 received from a fluid quality measurement device 100 can be compared to previously recorded fingerprints related to known good fluid quality. In some embodiments, this can be accomplished by separating known good fluid types by clustering the recorded fingerprints in the feature space, and then calculating a suitable distance metric to indicate how much the current fluid quality differs from known good conditions.

The server 400 may also collect fluid sample fingerprints and/or holograms of microscopic objects from a number of fluid quality measurement devices 100 installed in various locations. The ability to collect large amounts of various kinds of holograms can be important for training the neural networks used in the fluid quality measurement device 100.

Figure 6:
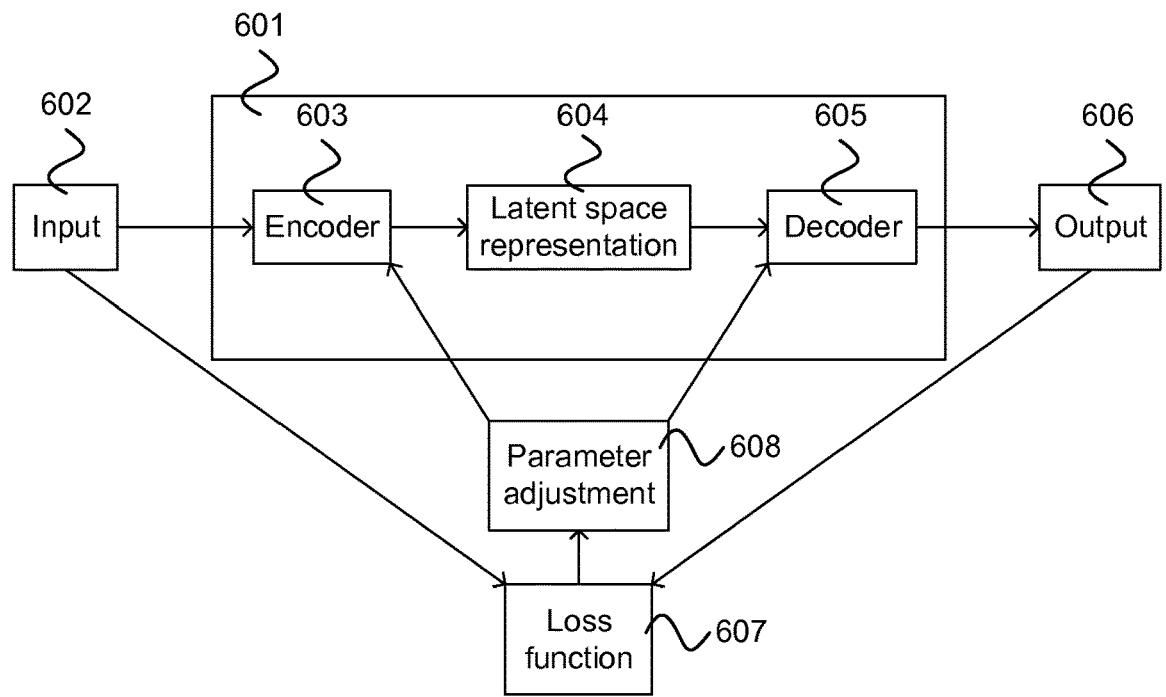
FIG. 6 illustrates a schematic representation of autoencoder neural network training according to an embodiment.

FIG. 6 illustrates a schematic representation of autoencoder neural network (NN) training according to an embodiment.

The following discloses only a simplified example of the training of the autoencoder NN. As a person skilled art can appreciate, many aspects of neural network training can be implemented in various ways, and the current disclosure presents only examples of these without limiting the disclosure to those examples.

An autoencoder NN 601 comprises an encoder 603 comprising neural network and a decoder 605 comprising a neural network. The encoder 603 generates a latent space representation 604 of an input 602. The encoding performed by the encoder 603 can reduce the dimensionality of the input 602. For example, a hologram of a microscopic object can be encoded into a latent space representation of less than ten dimensions. The decoder 605, on the other hand, generates an output 606 based on the latent space representation 604.

The dimensionality reduction performed by the encoder 603 can be interpreted as data compression where the encoder 603 compresses the input 602 from the initial space to the latent space. The decoder 605, on the other hand, decompresses the data from the latent space representation 604 to the output 606. The compression performed by the encoder 603 can be lossy, meaning that a part of the information comprised in the input 602 is lost during the encoding and cannot be fully recovered by the decoder 605.

During training of the autoencoder NN 601, a loss function 607 can be used to compute a loss between the input 602 and the output 606. The loss function 607 may comprise, for example, mean-squared error or perceptual loss between the input 602 and the output 606. The loss can represent how dissimilar the input 602 and output 606 are from each other, the value of the loss function 607 typically increasing the more dissimilar the input 602 and the output 606 are. Thus, the loss can be used as a measurement of how well the decoder 605 can recover the input 602 from the latent space representation 604 generated by the encoder 603. Based on the loss, parameters of the autoencoder NN 601, such as parameters of the neural networks in the encoder 603 and in the decoder 605, can be adjusted 608 in order to minimise the loss. This can be repeated in an iterative manner until the autoencoder NN 601 can perform the required task with sufficient accuracy.

Since an autoencoder NN 601 can be trained based on the input 602 and the output 606 using an appropriate loss function 607, the training does not require large quantities of labelled training data. Rather, the autoencoder NN 601 can be trained in an unsupervised manner. Thus, when used to detect microscopic objects in fluid samples, an autoencoder NN 601 can learn to generate the latent space representation 604 of the holograms of the microscopic objects without the need to provide explicit labels for the microscopic objects during training.

Training enables automatic tuning of autoencoder NN 601 in order to extract features from a large and complex particle hologram dataset. Unlike traditional "hand tuned" computer vision algorithms, the autoencoder NN 601 is able to take into account all physical features visible in holograms of microscopic objects, not just explicitly hand-picked features, just as size or symmetry. Furthermore, different orientations of complex object shapes do not constitute a problem for the autoencoder NN.

According to an embodiment, the autoencoder NN 601 comprises a variational autoencoder neural network. A variational autoencoder NN is an autoencoder NN whose encodings distribution is regularised during the training in order to ensure that its latent space has such properties that the dimensions of the latent space encode information independently from each other. Instead of encoding an input as a single point in the latent space, a variational autoencoder NN encodes an input as a distribution over the latent space. The latent space representation generated by a variational autoencoder NN can be more regular and therefore more stable.

According to an embodiment, the autoencoder NN 601 comprises a convolutional variational autoencoder neural network. Convolutional variational autoencoder neural networks can utilise convolutional neural network layers in the encoder 603 and/or in the decoder 605. A convolutional layer can perform convolution operations between the input of the layer and a kernel/filter of the layer.

Figure 7:
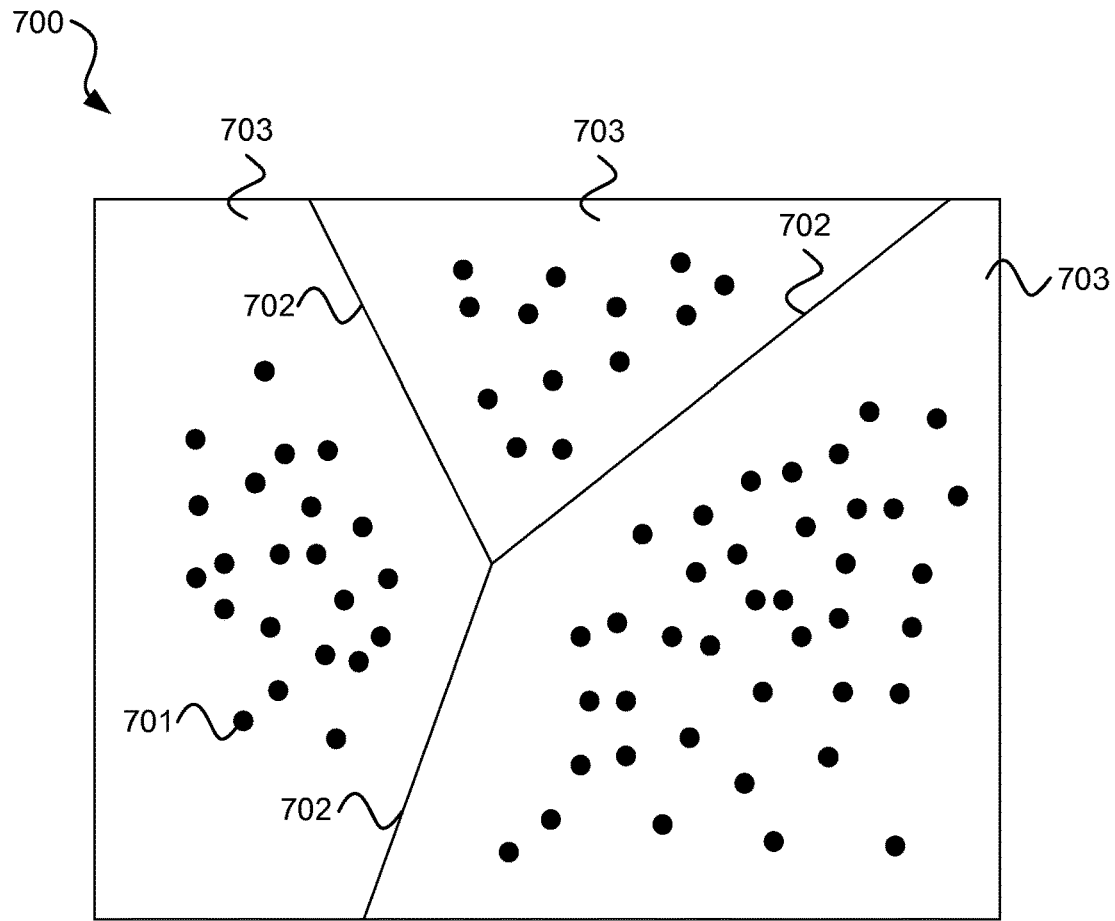
FIG. 7 illustrates a schematic representation of a latent space partitioning according to an embodiment.

FIG. 7 illustrates a schematic representation of latent space partitioning according to an embodiment.

The embodiment of FIG. 7 only illustrates latent space partitioning in a simplified manner. In practical situations, the dimensionality of the latent space may be greater, and the partitions formed in the latent space may be more complex than what is illustrated in the embodiment of FIG. 7.

After the autoencoder NN 601 has been trained, experimental data and a suitable clustering algorithm can be used to partition the latent space 700 in an unsupervised manner. The clustering algorithm may comprise, for example, k-means clustering or any other appropriate clustering algorithm. The clustering algorithm can define a set of boundaries 702 in the latent space 700 so that the latent space representations of holograms 701 in each partition 703 represent a different kind of micro object detected in a fluid sample.

Based on large amounts of experimental data, initial latent space partitions can be combined (agglomerated), adjusted and/or added to get an optimized set of partitions 703. Each such partition 703 can correspond to a class. The partitions 703 can be saved, for example, into the memory 102 of the fluid quality measurement device 100. Thus, during operation, the fluid quality measurement device 100 can detect the number of microscopic objects within these partitions 703 and produce the fluid sample fingerprint.

In some embodiments, the fluid quality measurement device 100 can utilise both agglomerated and non-agglomerated partitions 703. The fluid quality measurement device 100 may detect rare microscopic objects that may indicate fluid contamination even in small concentrations using the non-agglomerated partitions, while using the agglomerated partitions for detecting more typical microscopic objects.

In the embodiment of FIG. 7, the latent space representations of the holograms 701 form three clusters. Thus, the clustering algorithm has divided the latent space into three partitions 703.

Although the latent space representation of holograms 701 are illustrated as points in the embodiment of FIG. 7, the latent space representations 701 may take also other forms, such as distributions in the case of a variational autoencoder NN.

The training of the autoencoder NN 601 and the partitioning of the latent space 700 can be performed with any computing device. The trained autoencoder NN 601 and the latent space partitions 703 can be deployed into one or more fluid quality measurement devices 100 to be used in for fluid quality monitoring by, for example, saving corresponding models in the memory 102 of the fluid quality measurement devices 100.

As the server 400 gathers more data, such as fluid sample fingerprints, sample holograms, and/or latent space representations of sample hologram, from one or more fluid quality measurement devices 100, the gathered data may be used for further training of the autoencoder NN 601 and for optimising the latent space partitions 703 further. Such further training and optimisation may be performed by, for example, the server 400 or by some other computing device that can obtain the data from the server 400. The retrained autoencoder NN 601 and the optimised latent space partitions 703 can be deployed by, for example, the server 400 via, for example, over-the-air (OTA) updates to the one or more fluid quality measurement devices 100.

Figure 8:
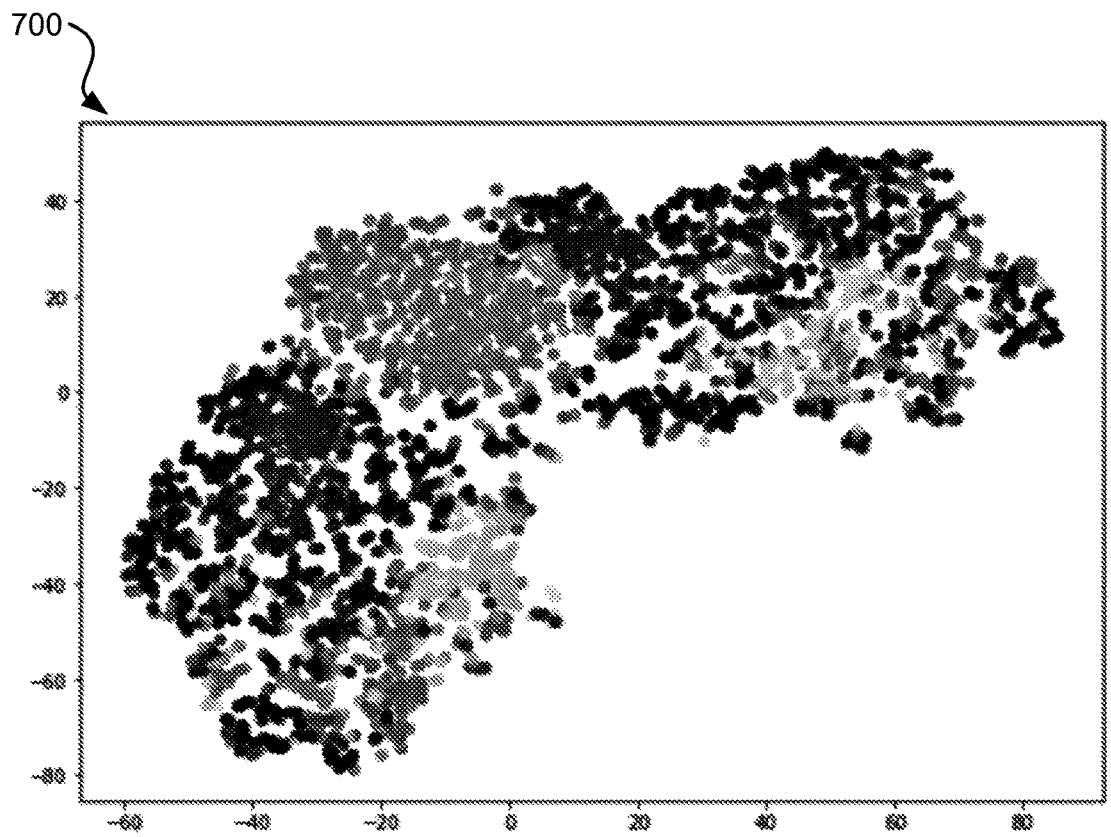
FIG. 8 illustrates a plot representation of a two-dimensional projection of a latent space comprising latent space representations of holograms according to an embodiment.

FIG. 8 illustrates a plot representation of a two-dimensional projection of a latent space 700 comprising latent space representations of holograms according to an embodiment.

Each point in FIG. 8 corresponds to a latent space representation of a hologram. It should be appreciated that although the dimensionality of the latent space 700 can be greater, only two dimensions can be represented in FIG. 8. Thus, it is not feasible to clearly illustrate the latent space partitions in such a figure. The latent space 700 may comprise, for example, less than ten dimensions, such as 6-8 dimensions.

Based on the representation of each hologram in the latent space, the fluid quality measurement device 100 can associate each hologram with a latent space partition. The latent space partitions may have been formed by a clustering algorithm as disclosed herein. In the embodiment of FIG. 8, latent space representations of holograms corresponding to different partitions are illustrated with different shades of grey. Each latent space partition can correspond to a different class. Thus, based on the number of holograms in each cluster, the fluid quality measurement device 100 can compute a concentration of microscopic objects in each class in the fluid sample.

Figure 9:
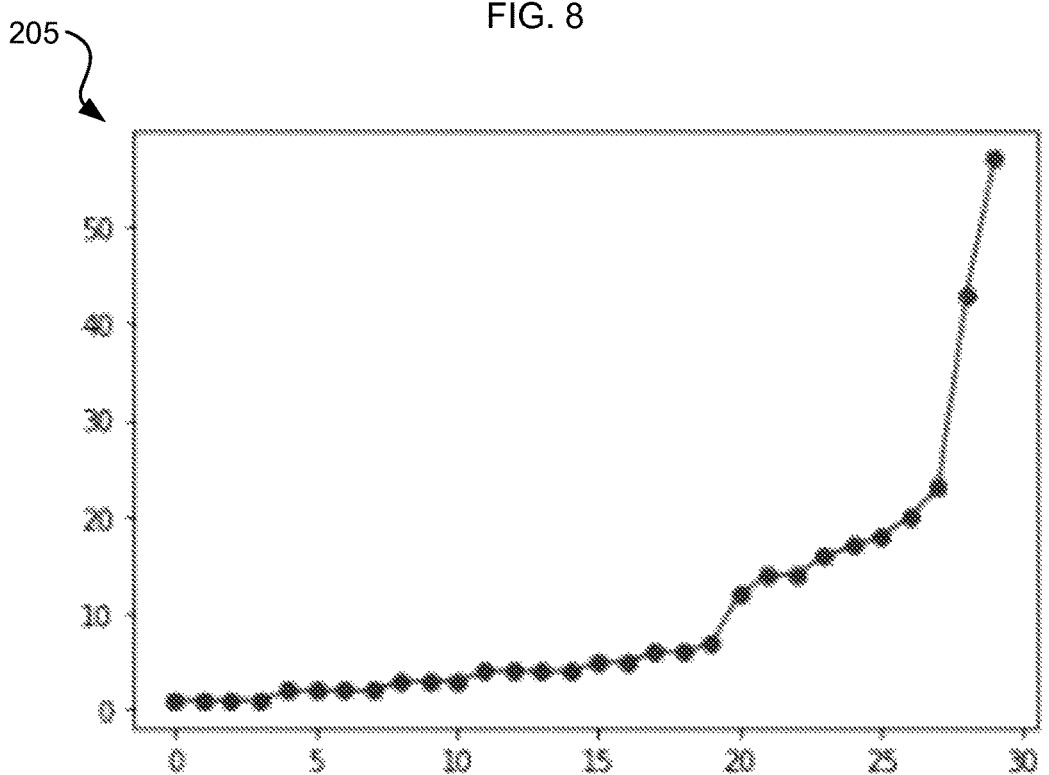
FIG. 9 illustrates a plot representation of a fluid sample fingerprint according to an embodiment.

FIG. 9 illustrates a plot representation of a fluid sample fingerprint 205 according to an embodiment.

The fluid sample fingerprint 205 in the embodiment of FIG. 9 comprises 30 classes and the number of detected microscopic objects for each class.

A fluid sample fingerprint 205 can comprise an indication of a concentration microscopic objects in each class in the fluid sample. For example, in the embodiment of FIG. 9, the fluid sample fingerprint 205 comprises the number of microscopic objects detected in each class. The concentration can be computed, by for example the fluid quality measurement device 100 and/or the server 400, when the volume of the fluid sample is known. Alternatively, all computations may be performed using the number of detected microscopic objects instead of the concentration.

Figure 10:
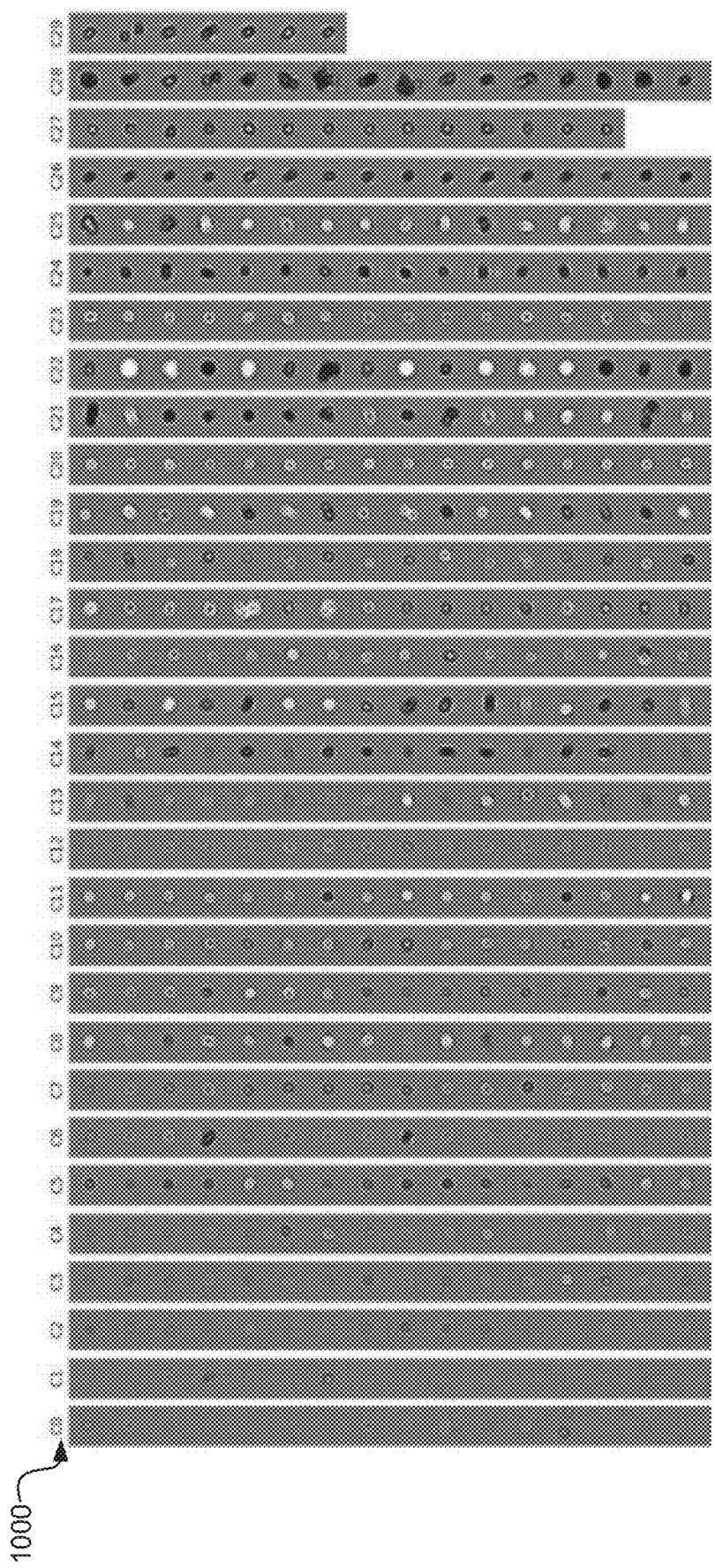
FIG. 10 illustrates a schematic representation of two-dimensional images of microscopic objects corresponding to different classes according to an embodiment.

FIG. 10 illustrates a schematic representation of two-dimensional images of microscopic objects corresponding to different classes according to an embodiment.

The classes 1000 illustrated in the embodiment of FIG. 10 correspond to the classes of the embodiments of FIG. 8 and FIG. 9. Thus, the classes 1000 have been obtained based on the latent space representations produced by the autoencoder NN.

The above-described process of producing the fluid sample fingerprint based from the plurality of holograms compresses the current state of the fluid sample into the fluid sample fingerprint. This provides a holistic view of the state of the fluid sample. However, the smallest concentrations of rare but interesting microscopic objects, such as fibres, can go unnoticed by observing solely the fluid sample fingerprint.

The fluid quality measurement device 100 can solve this by utilising image recognition performed with a convolutional neural network (CNN) in addition to the autoencoder NN 601.

According to an embodiment, the fluid quality measurement device 100 is further configured to assign each hologram in the plurality of holograms to a class in a second plurality of classes using a trained convolutional neural network (CNN), wherein the second plurality of classes comprises at least one class of interest.

The CNN may be trained in a supervised manner to recognize microscopic objects corresponding to classes of interest.

In supervised learning, the CNN may be trained to map an input to an output based on training data comprising example input-output pairs. The input may be a hologram and the output may be a class to which the microscopic object represented by the hologram belongs. After training, the CNN can assign a class for holograms that were not in the training data but that resemble examples in the training data.

The at least one class of interest may correspond to, for example, microscopic objects that should be detected even in low concentrations. These microscopic objects may be referred to as indicator particles. Such microscopic object may comprise, for example, microscopic objects that can cause the fluid to be unsuitable for drinking even in small concentrations.

The fluid quality measurement device 100 may be further configured to compute an indication of a concentration of microscopic objects corresponding to the at least one class of interest in the fluid sample based on the assignment of the plurality of holograms into the second plurality of classes.

In some embodiments, the fluid quality measurement device 100 may be configured to compute an indication of a concentration of microscopic objects for each class in the second plurality of classes. In other embodiments, the fluid quality measurement device 100 may be configured to compute an indication of the concentration of microscopic objects corresponding to the at least one class of interest.

The fluid quality measurement device 100 may be further configured to provide the indication of the concentration of microscopic objects corresponding to the at least one class of interest in the fluid sample for transmission to the server and/or provide the indication of the concentration of microscopic objects corresponding to the at least one class of interest in the fluid sample to a user.

The fluid quality measurement device 100 may, for example, provide the indication of the concentration using the fluid sample fingerprint or the fluid quality measurement device 100 may transmit the indication of the concentration separately from the fluid sample fingerprint.

The CNN and the autoencoder NN can provide two levels of analysis. The autoencoder NN can learn complex, unstructured and unlabelled patterns generally present in the microscopic object data, providing a reliable clustering and stability. The CNN adds to this an overview by identifying rare microscopic objects that, due to their scarcity (e.g. $1/10^5$ objects) go otherwise unnoticed. By utilising both NN types, the fluid quality measurement device 100 can provide a holistic and robust assessment of the microscopic object concentrations in the fluid sample.

Figure 11:
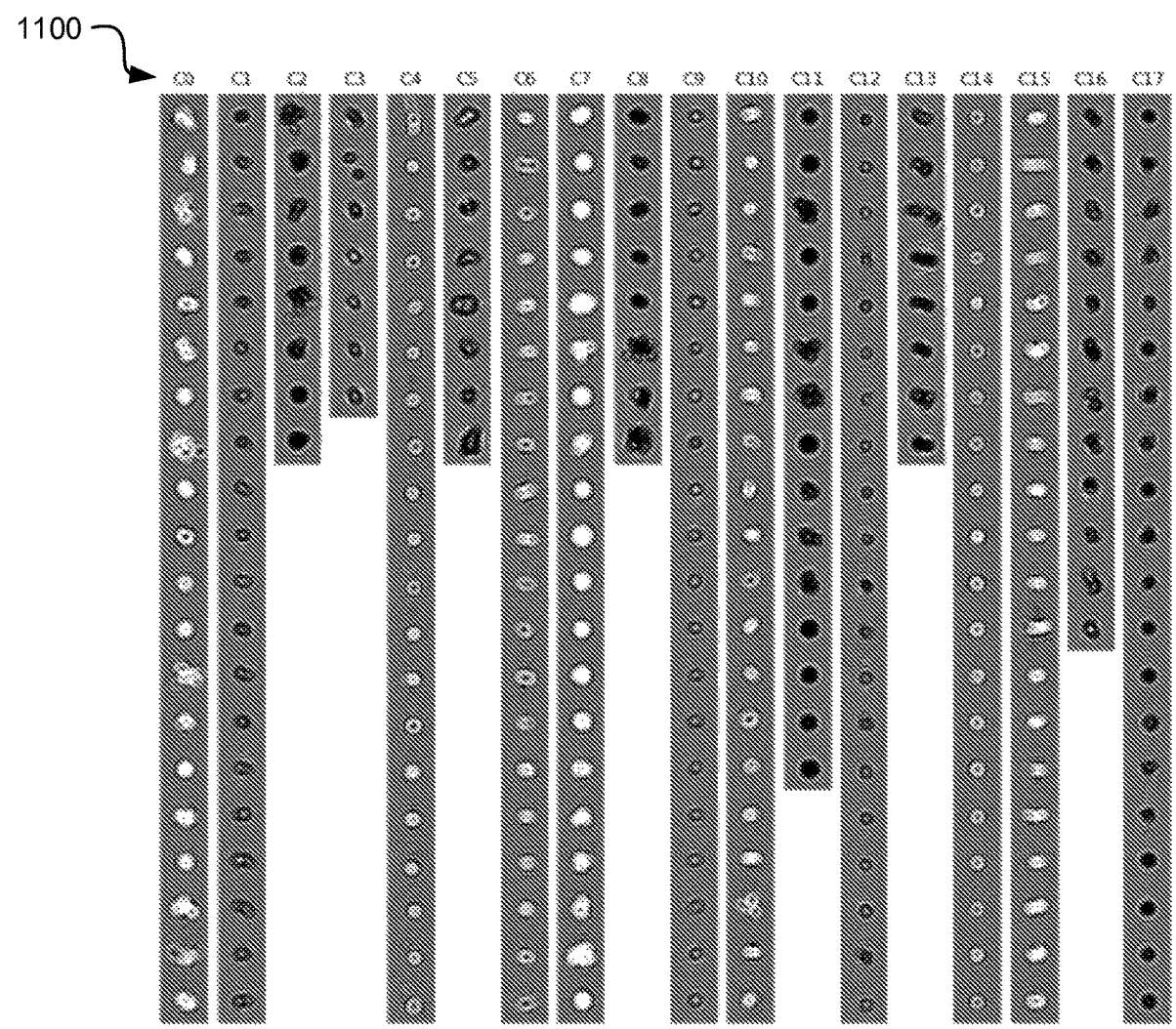
FIG. 11 illustrates a schematic representation of two-dimensional images of microscopic objects corresponding to different classes according to another embodiment.

FIG. 11 illustrates a schematic representation of two-dimensional images of microscopic objects corresponding to different classes according to another embodiment.

The classes 1100 illustrated in the embodiment of FIG. 11 may correspond to rare microscopic objects. The fluid quality measurement device 100 may detect such rare microscopic objects using, for example, the CNN or the autoencoder NN and non-agglomerated latent space partitions.

Figure 12:
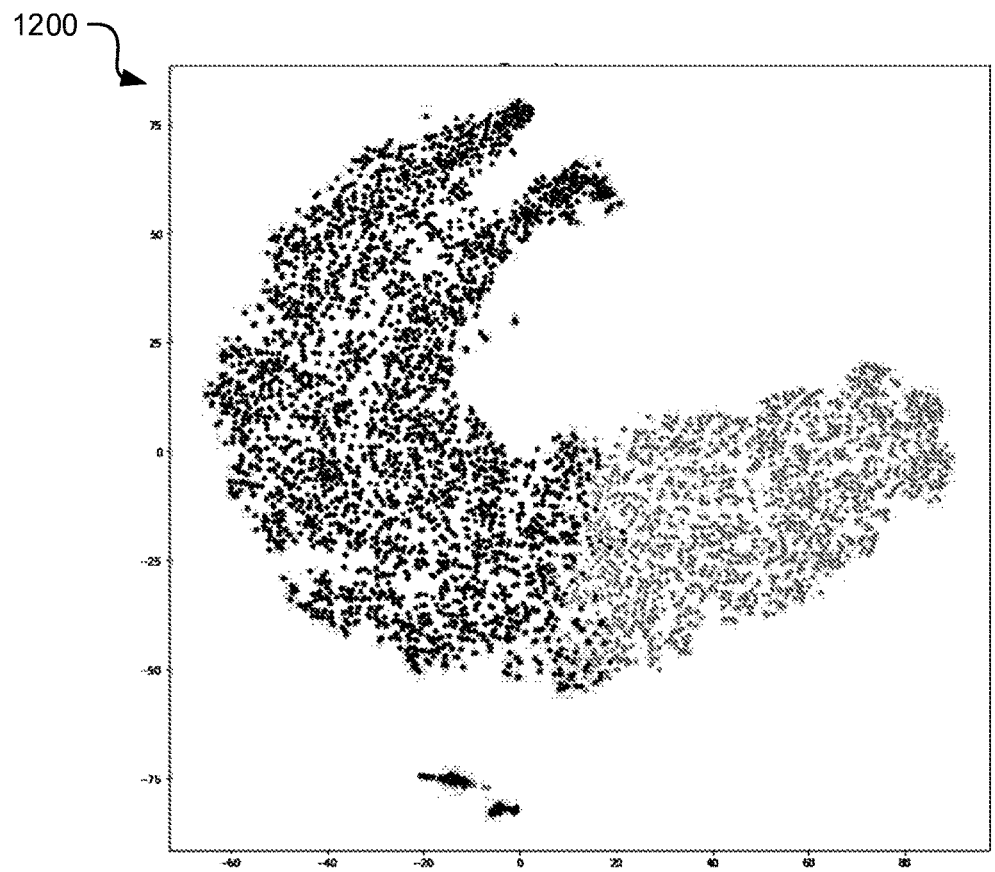
FIG. 12 illustrates a plot representation of a plurality of fluid sample fingerprints in feature space according to an embodiment.

FIG. 12 illustrates a plot representation of a plurality of fluid sample fingerprints in feature space.

It should be appreciated that only two dimensions of the feature space can be illustrated in FIG. 12 even though the dimensionality of the feature space can be significantly greater. For example, the number of dimensions in the feature space may be equal to the number of classes in the fluid sample fingerprint.

Each dot in FIG. 12 represented a fluid sample fingerprint. The server 400 may use a feature space representation similar to that illustrated in the embodiment of FIG. 12 in order to assess fluid quality as disclosed herein.

Figure 13:
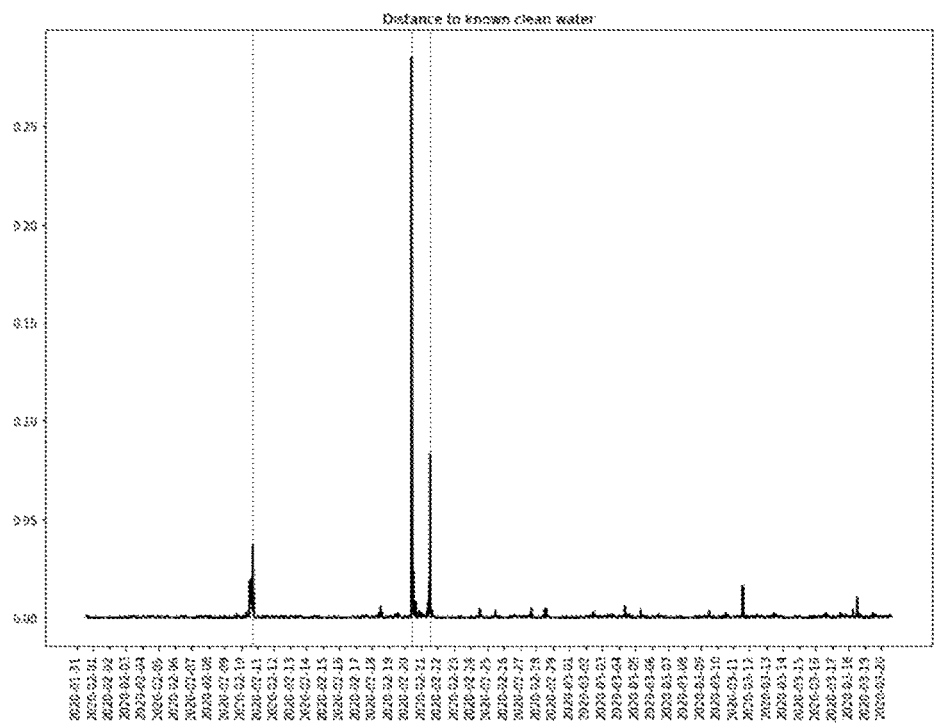
FIG. 13 illustrates a plot representation of distance between a reference fingerprint and fluid sample fingerprints received from a fluid quality measurement device as a function of time according to an embodiment.

FIG. 13 illustrates a plot representation of distance metric between a reference fingerprint and fluid sample fingerprints received from a fluid measurement device as a function of time.

The server 400 may receive fluid sample fingerprints from the fluid quality measurement device over time, for example periodically. For each such fluid sample fingerprint, the server 400 can calculate a distance metric between the fluid sample fingerprint and a reference fingerprint as disclosed herein. The embodiment of FIG. 13 illustrates how such a distance metric may vary as a function of time. In the embodiment of FIG. 13, the plot corresponding to the distance metric has been filtered using a mean smoothing filter. The three largest spikes visible in the plot of FIG. 13 correspond to time instances at which contaminants were added to the fluid sample.

Each time the server 400 computes the distance metric, the server 400 can compare the computed distance metric to a preconfigured maximum distance metric. If the distance metric is greater than the maximum distance metric, the server 400 may provide an anomaly notification. For example, in the case of the embodiment of FIG. 13, if the maximum distance metric was set to 0.1, the server 400 would provide an anomaly notification at the time of the largest peak illustrated in FIG. 13.

Figure 14:
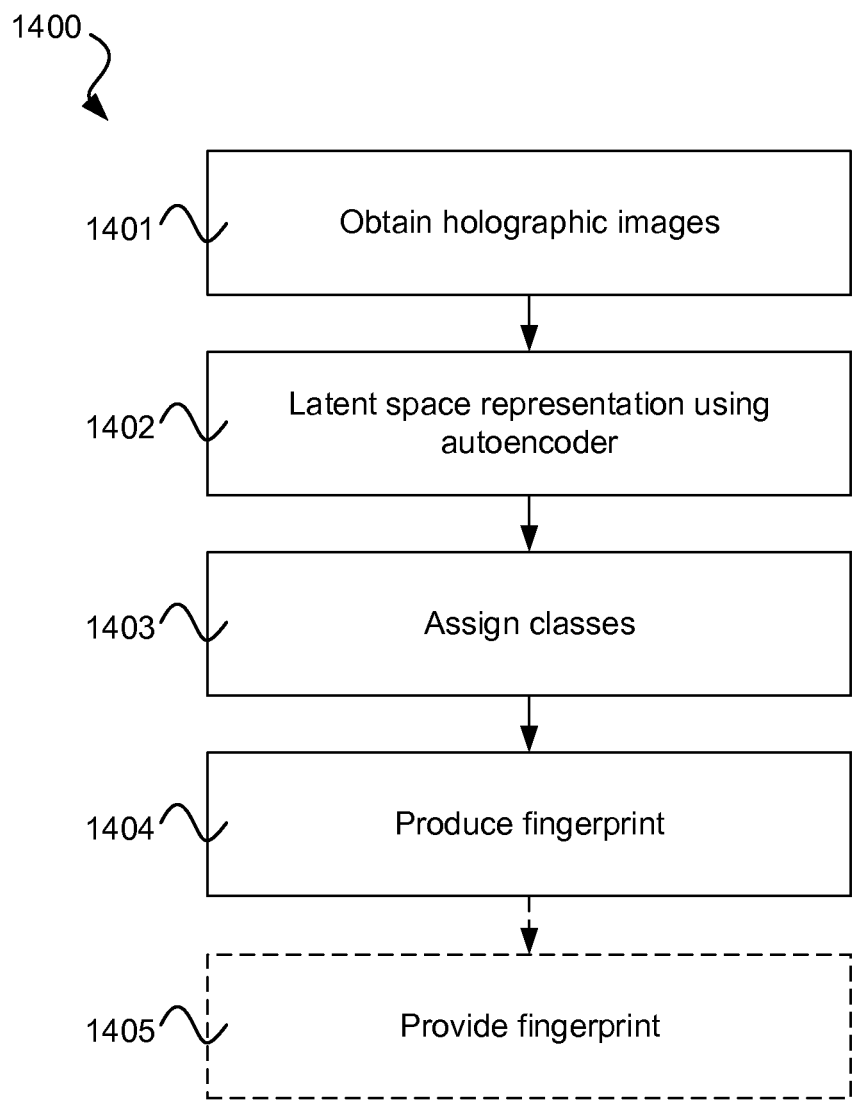
FIG. 14 illustrates a flow chart representation of a method for fluid quality measurement according to an embodiment.

FIG. 14 illustrates a flow chart representation of a method 1400 for fluid quality measurement.

According to an embodiment, the method 1400 comprises obtaining 1401 a plurality of holograms, wherein each hologram in the plurality of holograms represents a microscopic object in a fluid sample.

The method 1400 may further comprise producing 1402 a latent space representation of each hologram in the plurality of holograms using a trained autoencoder neural network.

The method 1400 may further comprise assigning 1403 each hologram in the plurality of holograms to a class in a plurality of classes based on the latent space representation of the hologram, wherein each class in the plurality of classes corresponds to a partition of the latent space.

The method 1400 may further comprise producing 1404 a fluid sample fingerprint based on the assignment of the plurality of holograms into the plurality of classes, wherein the fluid sample fingerprint comprises an indication of a concentration of microscopic objects in the fluid sample for each class in the plurality of classes; and The method 1400 may further comprise providing 1405 the fluid sample fingerprint for transmission to a server and/or providing the fluid sample fingerprint to a user.

The method 1400 may be performed by, for example, the fluid quality measurement device 100.

Figure 15:
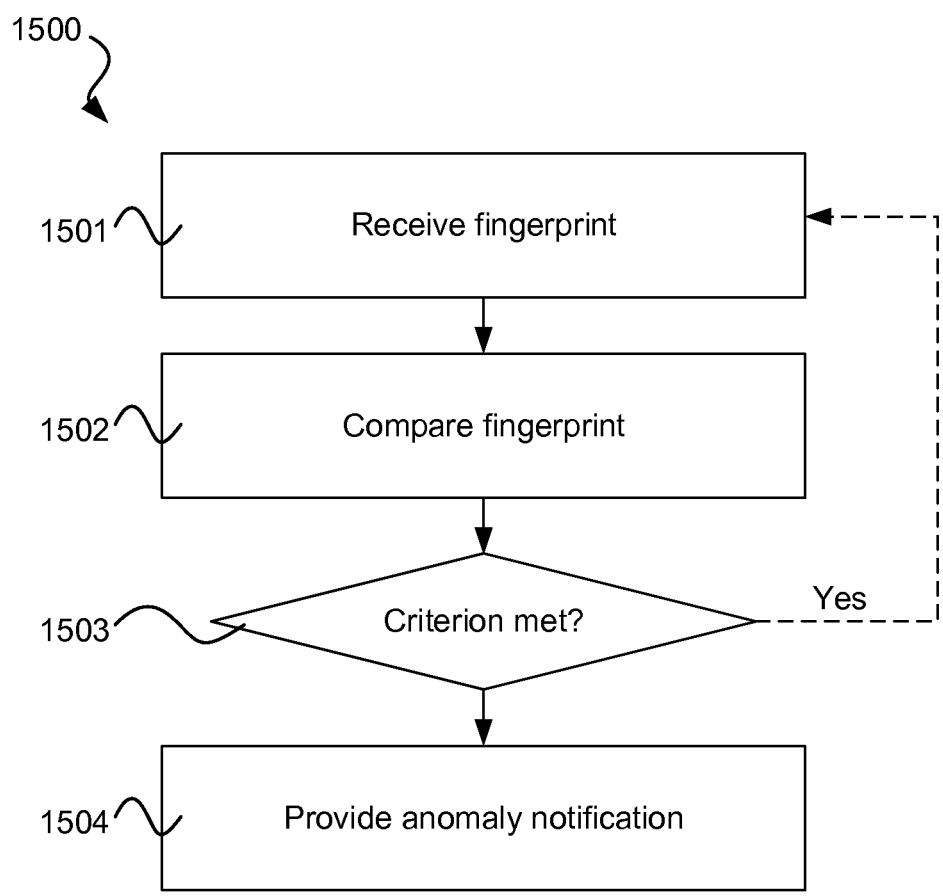
FIG. 15 illustrates a flow chart representation of a method for fluid quality monitoring according to an embodiment.

FIG. 15 illustrates a flow chart representation of a method 1400 for fluid quality monitoring according to an embodiment.

According to an embodiment, the method 1400 comprises receiving 1501 a fluid sample fingerprint from a fluid quality measurement device, wherein the fluid sample fingerprint comprises an indication of a concentration of microscopic objects in a fluid sample for each class in a plurality of classes.

The method 1500 may further comprise comparing 1502 the fluid sample fingerprint to at least one preconfigured criterion.

The method 1500 may further comprise, in response to the fluid sample fingerprint not meeting 1503 the preconfigured criterion, providing 1504 an anomaly notification.

If the criterion is met, the method may return to operation 1501 in order to receive a new fluid sample fingerprint.

The method 1500 may be performed by, for example, the server 400.

Any range or device value given herein may be extended or altered without losing the effect sought. Also any embodiment may be combined with another embodiment unless explicitly disallowed.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item may refer to one or more of those items.

The steps of the methods described herein may be carried out in any suitable order, or simultaneously where appropriate. Additionally, individual blocks may be deleted from any of the methods without departing from the spirit and scope of the subject matter described herein. Aspects of any of the embodiments described above may be combined with aspects of any of the other embodiments described to form further embodiments without losing the effect sought.

The term 'comprising' is used herein to mean including the method, blocks or elements identified, but that such blocks or elements do not comprise an exclusive list and a method or apparatus may contain additional blocks or elements.

It will be understood that the above description is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification.

The invention claimed is:

1. A fluid quality measurement device, comprising:
   at least one processor; and
   at least one memory including computer program code;
   the at least one memory and the computer program code configured to, with the at least one processor, cause the fluid quality measurement device to:
   obtain a plurality of holograms, wherein each hologram in the plurality of holograms represents a microscopic object in a fluid sample;
   produce a latent space representation of each hologram in the plurality of holograms using a trained autoencoder neural network;
   assign each hologram in the plurality of holograms to a class in a plurality of classes based on the latent space representation of the hologram, wherein each class in the plurality of classes corresponds to a partition of the latent space; and
   produce a fluid sample fingerprint based on the assignment of the plurality of holograms into the plurality of classes, wherein the fluid sample fingerprint comprises an indication of a concentration of microscopic objects in the fluid sample for each class in the plurality of classes.

2. The fluid quality measurement device according to claim 1, wherein the at least one memory and the computer program code are further configured to, with the at least one processor, cause the fluid quality measurement device to:
   provide the fluid sample fingerprint for trans-mission to a server; and/or
   provide the fluid sample fingerprint to a user.

3. The fluid quality measurement device according to claim 1, wherein the autoencoder neural network comprises a variational autoencoder neural network or a convolutional variational autoencoder neural network.

4. The fluid quality measurement device according to claim 1, wherein the at least one memory and the computer program code are further configured to, with the at least one processor, cause the fluid quality measurement device to:
provide a sample hologram from the plurality of holograms for at least one class in the plurality of classes for transmission to a server; and/or
provide a sample hologram from the plurality of holograms for at least one class in the plurality of classes to a user.

5. The fluid quality measurement device according to claim 1, wherein the at least one memory and the computer program code are further configured to, with the at least one processor, cause the fluid quality measurement device to provide a sample latent space representation of a hologram from the plurality of holograms for at least one class in the plurality of classes for transmission to a server.

6. The fluid quality measurement device according to claim 1, wherein the at least one memory and the computer program code are further configured to, with the at least one processor, cause the fluid quality measurement device to:
assign each hologram in the plurality of holo-grams to a class in a second plurality of classes using a trained convolutional neural network, where-in the second plurality of classes comprises at least one class of interest; and
compute an indication of a concentration of microscopic objects corresponding to the at least one class of interest in the fluid sample based on the assignment of the plurality of holograms into the second plurality of classes.

7. The fluid quality measurement device according to claim 6, wherein the at least one memory and the computer program code are further configured to, with the at least one processor, cause the fluid quality measurement device to:
provide the indication of the concentration of microscopic objects corresponding to the at least one class of interest in the fluid sample for transmission to a server; and/or
provide the indication of the concentration of microscopic objects corresponding to the at least one class of interest in the fluid sample to a user.

8. The fluid quality measurement device according to claim 1, further comprising an imaging unit configured to produce the plurality of holograms using digital holographic microscopy.

9. A server comprising:
at least one processor; and
at least one memory including computer program code;
the at least one memory and the computer program code configured to, with the at least one processor, cause the server to:
receive a fluid sample fingerprint from a fluid quality measurement device, wherein the fluid sample fingerprint comprises an indication of a concentration of microscopic objects in a fluid sample for each class in a plurality of classes;
compare the fluid sample fingerprint to at least one preconfigured criterion;
in response to the fluid sample fingerprint not meeting the preconfigured criterion, provide an anomaly notification.

10. The server according to claim 9, wherein the at least one memory and the computer program code are further configured to, with the at least one processor, cause the server to compare the fluid sample fingerprint to at least one preconfigured criterion by performing:
produce a feature space representation of the fluid sample fingerprint, wherein each dimension of the feature space corresponds to a class in the plurality of classes; and
compare the feature space representation of the fluid sample fingerprint to a feature space representation of at least one reference fingerprint.

11. The server according to claim 10, wherein the at least one memory and the computer program code are further configured to, with the at least one processor, cause the server to compare the feature space representation of the fluid sample fingerprint to a feature space representation of the at least one reference fingerprint by calculating a distance metric between the fluid sample fingerprint and the at least one reference fingerprint.

12. The server according to claim 11, wherein the at least one memory and the computer program code are further configured to, with the at least one processor, cause the server to:
compare the calculated distance metric to a preconfigured maximum distance metric; and
in response to the calculated distance metric being greater than the preconfigured maximum distance metric, provide the anomaly notification.

13. The server according to claim 9, wherein the at least one memory and the computer program code are further configured to, with the at least one processor, cause the server to compare the fluid sample fingerprint to at least one preconfigured criterion by performing:
compare the indication of the concentration of microscopic objects in the fluid sample of each class in the plurality of classes to a corresponding preconfigured maximum value; and
in response to the indication of the concentration of microscopic objects being greater than the corresponding preconfigured maximum value in at least one class, provide the anomaly notification.

14. A fluid monitoring system comprising at least one fluid quality measurement device according to claim 1 and a server according to claim 9.

15. A method for fluid quality measurement, the method comprising:
obtaining a plurality of holograms, wherein each hologram in the plurality of holograms represents a microscopic object in a fluid sample;
producing a latent space representation of each hologram in the plurality of holograms using a trained autoencoder neural network;
assigning each hologram in the plurality of holograms to a class in a plurality of classes based on the latent space representation of the hologram, wherein each class in the plurality of classes corresponds to a partition of the latent space; and
producing a fluid sample fingerprint based on the assignment of the plurality of holograms into the plurality of classes, wherein the fluid sample fingerprint comprises an indication of a concentration of microscopic objects in the fluid sample for each class in the plurality of classes.

16. A method for fluid quality monitoring, the method comprising:

receiving a fluid sample fingerprint from a fluid quality measurement device, wherein the fluid sample fingerprint comprises an indication of a concentration of microscopic objects in a fluid sample for each class in a plurality of classes;

comparing the fluid sample fingerprint to at least one preconfigured criterion;

in response to the fluid sample fingerprint not meeting the preconfigured criterion, providing an anomaly notification.

17. A computer program product comprising program code configured to perform the method according to claim 15 when the computer program product is executed on a computer.

18. A computer program product comprising program code configured to perform the method according to claim 16 when the computer program product is executed on a computer.

* * * * *